United States Patent [19]

Behrenz et al.

[11] Patent Number: 4,845,131
[45] Date of Patent: Jul. 4, 1989

[54] AGENTS FOR COMBATING *TINEOLA BISELLIELLA*

[75] Inventors: Wolfgang Behrenz, Overath, Fed. Rep. of Germany; Gianfranco Salvetti, Mailand, Italy

[73] Assignee: Bayer Aktiengesellschaft, Leverkusen, Fed. Rep. of Germany

[21] Appl. No.: 170,502

[22] Filed: Mar. 18, 1988

[30] Foreign Application Priority Data

Apr. 8, 1987 [DE] Fed. Rep. of Germany ....... 3711910

[51] Int. Cl.$^4$ .................... A01N 31/00; A61K 31/045
[52] U.S. Cl. .................................................. 514/729
[58] Field of Search .................. 514/729, 918, 919; 424/DIG. 10

[56] References Cited

U.S. PATENT DOCUMENTS 4,233,161 11/1980 Sato et al. .................. 424/DIG. 10
4,735,358  4/1988 Morita et al. ............................ 239/1

FOREIGN PATENT DOCUMENTS 0803178 10/1958 United Kingdom .

OTHER PUBLICATIONS

Burton–"Intrinsic Mosquito Repellency Values of Some Chemical Compounds", Amer Perfumer and Cosmetics (84) pp. 41–44, (1969).
Takai et al.–"Synthesis of α-Pinene Analogs and their Biological Activity", Chem Abs (82) 86420q (1975).

*Primary Examiner*—Douglas W. Robinson
*Assistant Examiner*—Roger Gobrogge
*Attorney, Agent, or Firm*—Sprung Horn Kramer & Woods

[57] ABSTRACT

A method of combating clothes moths which comprises placing adjacent clothes to be protected from said moths or placing in a container for storing such clothes a clothes-moth-combatting effective amount of isoborneol of the formula

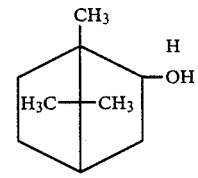

1 Claim, No Drawings

AGENTS FOR COMBATING *TINEOLA BISELLIELLA*

The present invention relates to the use of the known chemical compound isoborneol as an active compound against clothes moths.

Isoborneol has the structure

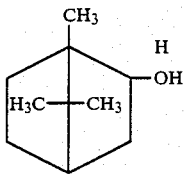

and the following spatial formula:

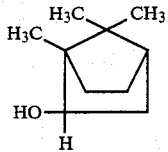

and is a chemical compound which has been known for a long time. It is optically active and can be in the form of various stereoisomers or in the form of the DL-racemate. DL-Isoborneol has a melting point of 212° C. and forms colorless crystals.

According to Ullmann's Encyklopädie der technischen Chemie (Ullmann's Encyclopaedia of Industrial Chemistry), 3rd edition, Munich 1966, volume 17, page 33, isoborneol is scarcely used as such, and chiefly serves as an intermediate product for the preparation of camphor.

The clothes moth, Tineola biselliella, is a widespread pest which attacks and destroys keratin-containing products of animal origin and is therefore greatly dreaded as a textile pest. Paradichlorobenzene has hitherto been used on a wide scale for protection from eating by moths, and is placed amongst the textiles to be protected in cupboards and drawers in the form of so-called mothballs or moth powders. Paradichlorobenzene thereby develops vapors which kill the moths. However, the use of paradichlorobenzene as an agent for combating moths has recently been regarded as not being without problems for toxicological reasons.

It has been found that the known compound isoborneol of the formula

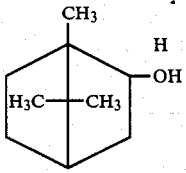

has a potent activity against clothes moths. Isoborneol can be used here as the DL-racemate or in the form of optical isomers.

Surprisingly, isoborneol exhibits a considerably more potent activity against clothes moths than paradichlorobenzene, the compound known from the prior art.

The provision of isoborneol as an agent against clothes moths thus represents an enrichment of the prior art.

The isoborneol which can be used according to the invention has a relatively specific, highly pronounced activity against the clothes moth (Tineola biselliela).

Isoborneol can be converted into the formulations customary for combating moths, such as solutions, emulsions, suspensions, powders, foams, pastes, granules, beads, tablets, aerosols, natural and synthetic substances impregnated with active compound, such as, for example, moth paper, very fine capsules in polymeric substances and in coating compositions, and furthermore in formulations used with burning equipment, such as fumigating cartridges, fumigating cans, fumigating coils and the like. Powders, granules, tablets, mothballs, moth cylinders, moth paper and aersols are preferably used.

These formulations are produced in known manner, for example by mixing the isoborneol with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Aroma substances, such as, for example, perfume oils, can also be added to the formulations.

The isoborneol-containing agents against clothes moths can be modified by the addition of substances which intensify the action, such as, for example, ethereal oils, which increase the vapor pressure of the preparation.

On the other hand, the period of activity of such formulations can be increased by addition of substances which reduce the vapor pressure, such as, for example, polyethylene glycols.

The formulations in general contain between 10 and 100% by weight of active compound, preferably between 40 and 100%, that is to say isoborneol pure substance, for example in powder or granule form, can also be used in the formulations.

The isoborneol which can be used according to the invention can be present in commercially available formulations and in the use forms prepared from these formulations as a mixture with other active compounds, such as insecticides, baits, sterilizing agents and fungicides. The insecticides include, for example, phosphoric acid esters, carbamates, carboxylic acid esters, chlorinated hydrocarbons, phenylureas, pyrethroids, substances prepared by microorganisms and the like.

For combating moths, the ready-to-use formulations are placed in closed-off spaces, preferably in clothes cupboards and laundry cupboards.

Some typical formulations are listed by way of example below.

1. Formulation example: Aerosol

An aerosol preparation was produced by mixing the following components: 5 g of D,L-iosborneol, 0.04 g of cyfluthrin (a pyrethroid), 14.46 g of acetone made up to 100 g with propane/butane propellant gas.

2. Formulation example: Aerosol

Another aerosol preparation was produced by mixing 5 g of D,L-isoborneol with 1 g of perfume oil and 14 g of acetone and subsequently making up the mixture to 100 g with propane/butane propellant gas.

3. Formulation example: Tablets 100 g of D,L-isoborneol are mixed with 5 g of magnesium stearate and the mixture is ground and pressed to tablets with a tabletting machine.

4. Formulation example: Tablets 90 g of D,L-isoborneol are mixed with 1 g of perfume oil and pressed to tablets with a tabletting machine.

5. Formulation example: Granules 100 g of D,L-isoborneol are mixed with 2.5 g of natural rock powder and 1 g of spindle oil and the mixture is treated in a mixer until homogeneous free-flowing, non-dusting granules are formed.

6. Formulation example: Granules 100 g of D,L-isoborneol are mixed with 1 g of perfume oil and the mixture is treated in a mixer until homogeneous free-flowing, non-dusting granules are formed.

7. Formulation example: Moth paper 10 g of D,L-isoborneol are dissolved in 90 ml of ethanol and the solution is applied to 1 m² of absorbent paper (paper weight 80–100 g per m²) by the gravure printing process. After the solvent has evaporated, the paper is ready to use.

The activity of the isoborneol which can be used according to the invention is illustrated by the following example.

Isoborneol, either pressed to a shaped article or in ground form, and for comparison paradichlorobenzene was introduced in watch glasses under Lang Welt bell jars of 19 Litres capacity placed on aluminum foil. The amounts of active compound were in all cases 850 mg/bell jar. 14 days later, a container which was closed with wire gauze and in which 10 clothes moth larvae in the 1st-2nd development stage were placed on woollen material was introduced under each bell jar. 10 butterflies were furthermore introduced into each bell jar through the top opening and the bell jars were then closed again. The destructive action on the butterfly moths was observed at initially relatively short and later longer intervals of time, and after 5 days the number of eggs laid was determined, and the eating damage caused to the woollen cloth by the moth larvae was ascertained after 7 days. The results have been summarized in the following table:

TABLE

| Hours$^h$ or days$^d$ | Action on adult clothes moths in hours or days after use in percent, number of eggs deposited and eating damage by the larvae | | |
|---|---|---|---|
| | Isoborneol in a shaped article | Isoborneol, finely ground | Paradichlorobenzene in a shaped article |
| $1^h$ | 5% | 45% | 0% |
| $1\frac{1}{2}^h$ | 25% | 55% | 0% |
| $2^h$ | 45% | 80% | 0% |
| $2\frac{1}{2}^h$ | 65% | 95% | 0% |
| $3^h$ | 75% | 100% | 0% |
| $4^h$ | 80% | | 0% |
| $5^h$ | 95% | | 0% |
| $24^h$ | 100% | | 35% |
| | 74 eggs no eating damage | 9 eggs no eating damage | 70%/159 eggs 6 holes eaten |

It will be understood that the specification and examples are illustrative but not limitative of the present invention and that other embodiments within the spirit and scope of the invention will suggest themselves to those skilled in the art.

What is claimed is:

1. A method of combating Tineola biselliella which comprises placing adjacent to the clothes to be protected therefrom or placing in a container for storing such clothes an amount effective therefor of isoborneol of the formula

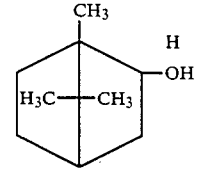

* * * * *